United States Patent [19]

Daiss et al.

[11] Patent Number: 4,933,291
[45] Date of Patent: Jun. 12, 1990

[54] CENTRIFUGABLE PIPETTE TIP AND PIPETTE THEREFOR

[75] Inventors: John L. Daiss, Rochester; Leonard J. Seaberg, Penfield; Alan J. Lowne, Victor, all of N.Y.

[73] Assignee: Eastman Kodak Company, Rochester, N.Y.

[21] Appl. No.: 95,693

[22] Filed: Sep. 14, 1987

Related U.S. Application Data

[63] Continuation-in-part of Ser. No. 944,778, Dec. 22, 1986, abandoned.

[51] Int. Cl.⁵ ............................................. G01N 35/00
[52] U.S. Cl. ........................................ 436/45; 436/177;
 422/72; 422/100; 422/101; 494/16; 494/17;
 494/19; 356/244; 356/246; 73/863.23;
 73/864.11; 73/864.13; 73/864.21
[58] Field of Search ........................... 422/72, 100, 101;
 436/45, 177; 494/16, 17, 19; 356/246, 244;
 73/863.23, 864.11, 864.13, 864.21

[56] References Cited

U.S. PATENT DOCUMENTS

| | | | |
|---|---|---|---|
| 3,880,592 | 4/1975 | Kelley et al. | 422/72 X |
| 3,882,716 | 5/1975 | Beimar | 494/19 X |
| 3,906,690 | 9/1975 | Amos et al. | 422/72 X |
| 3,953,172 | 4/1976 | Shapiro et al. | 422/72 X |
| 3,985,032 | 10/1976 | Avakian | 422/101 X |
| 4,244,916 | 1/1981 | Guigan | 422/72 |
| 4,624,835 | 11/1986 | Davis et al. | 422/102 |

Primary Examiner—Barry S. Richman
Assistant Examiner—Lynn M. Kummert
Attorney, Agent, or Firm—Dana M. Schmidt

[57] ABSTRACT

There are described a novel removable pipette tip and pipette therefor, which provide separation of substances of a liquid within the tip by centrifuging the tip. The tip comprises a liquid-confining cavity disposed about an axis of symmetry, a dispensing aperture, and separating structure spaced along the axis away from the dispensing aperture, for separating one of the liquid substances when the tip is spun about such axis. The pipette is rotatable and either the pipette or the analyzer includes a driver for spinning the pipette tip at high speed.

16 Claims, 7 Drawing Sheets

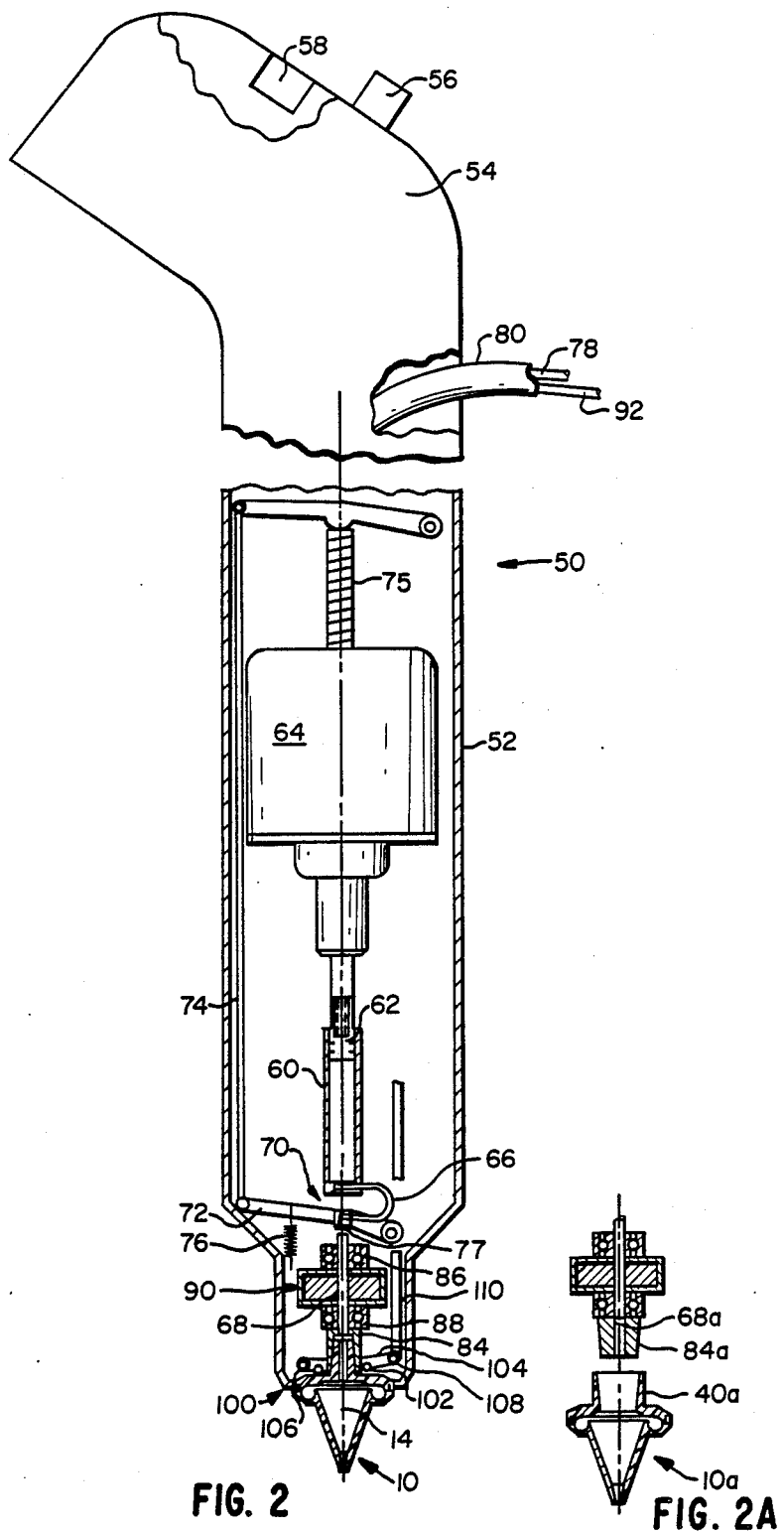

STOP SPIN

DISPENSE

CENTRIFUGABLE PIPETTE TIP AND PIPETTE THEREFOR

FIELD OF THE INVENTION

This invention relates to pipettes used to collect and dispense liquids, for example, liquids characterized by two phases of different densities.

BACKGROUND OF THE INVENTION

A large industry has developed around dried test elements used clinically to analyze serum or plasma for analytes that are a measure of a patient's health. Generally, such test elements have been designed exclusively for testing serum or plasma, in light of the fact that cells from whole blood cause interferences of various kinds. The drawback of such an approach is the necessity for centrifuging the patient sample first, to remove the unwanted blood cells. Conventionally, this has required the use of a separate centrifuge device and sample containers as well as separate operator involvement.

Such a centrifuge step has been only a minor inconvenience in those instances in which the test elements are used in hospitals or large laboratories. The reason is that such institutions have the equipment and expertise to readily perform the centrifuge separation step. However, the test elements and an appropriate analyzer have recently moved into the environment of the doctors' office. There, the need for a separate centrifuge step is a major drawback, since many doctors' offices lack the equipment and training to routinely do centrifuging prior to testing. Furthermore, the centrifuging step is time-consuming. Rapid testing is the essence of tests run in the doctors' office, in order to complete the diagnosis while the patient is still present.

Attempts have been made to convert so-called dried test elements used to analyze serum or plasma, into test elements useful also to test whole blood. Such attempts have featured the addition of a blood-cell filtering layer, above the spreading layer heretofore constituting the outermost layer. The purpose is to cause the cells to separate from the plasma, the cells being retained within the filter layer. In this way, the centrifuging step heretofore needed to obtain just serum or plasma from the whole blood, is eliminated. Examples are shown in EPO Application No. 0,159,727.

However, there are drawbacks to the approach using a blood-cell filtering layer. Chief of these is that there does not appear to be a single filter material that works for all the various test chemistries needed for the many different analytes. This may be partly due to the fact that some assays need to have reagents in the spreading layer (heretofore the outermost layer), and some have no reagents there. As a result, it has been difficult to obtain whole blood test elements for all the analytes currently tested in serum or plasma.

Therefore, prior to this invention there has been a need to provide test elements and analyzers that allow the direct testing of all analytes of whole blood, without requiring a preliminary blood cell separation step that involves separate equipment and operator involvement. Thus there is an important need, particularly in the doctors' office, is to provide a whole blood clinical analyzer for all analytes that is largely user transparent to the fact that some kind of cell-plasma separation step occurs during the process. (As used herein, "user transparent" means that the user involvement in achieving the noted step is minimal or non-existent.)

SUMMARY OF THE INVENTION

We have devised a pipette construction which provides for automatic separation of liquid components of a solution, dispersion or emulsion, such as cells from plasma, almost immediately upon collection of whole blood in the pipette tip. The features which make this possible are a novel pipette tip, a novel pipette, and optionally, a novel analyzer.

More specifically, in accord with one aspect of the invention there is provided a pipette tip capable of separating portions of a liquid solution, emulsion or dispersion, the tip comprising means for mounting the tip within a pipette, a body wall disposed about an axis of symmetry to define a liquid-confining cavity of the tip, means defining a dispensing aperture in the body wall, and separating means for separating, and maintaining separate, a first portion of the liquid solution, emulsion or dispersion from a second portion when the tip is spun about the axis.

In accord with another aspect of the invention, there is provided a pipette for aspirating and dispensing a liquid and having a fluid passageway cooperating with a pipette tip, first means for evacuating and pressurizing the fluid passageway for filling and dispensing such liquid from the tip, and means for removably mounting such tips. This pipette is improved in that the mounting means is constructed to permit the tips to rotate repeatedly at high speed about an axis of symmetry.

In accord with still another aspect of the invention, a combination of pipette and removable pipette tip is provided, the pipette having the axis, fluid passageway and first means described in the previous paragraph. This combination is improved in that the pipette further includes means for mounting the tip to rotate continuously on the pipette about the axis, and wherein the tip includes means for separating, and for maintaining separate, a portion of the liquid contained therein from the remainder in response to spinning at high speeds about the axis.

In accord with yet another aspect of the invention, there is optionally provided an analyzer comprising a first station constructed to dispense a body liquid onto a test element using a pipette provided with a pipette tip, a second read station including means for detecting a change in such test element in response to such body liquid, and means for transporting such test element from one of the stations to the other. The analyzer is improved in that the first station includes means for spinning the pipette tip at high speeds about an axis for symmetry.

Thus, it is an advantageous feature of the invention that whole blood is tested for analytes using test elements constructed for serum or plasma only, without requiring additional equipment used only for whole blood separation.

It is a related advantageous feature of the invention that whole blood is tested for analytes using test elements constructed for serum or plasma only, by equipment which is generally user transparent to the fact that a preliminary cell-plasma separation step takes place.

It is another advantageous feature of the invention that a pipette is provided that permits ready separation of a two-phase liquid having different-density phases, for uses other than dispensing plasma onto test elements.

Another advantageous feature of the invention is that components of a solution, an emulsion, or a dispersion can be separated by filtration within a pipette, with the filtered component being retained in position for subsequent treatment.

Other advantageous features will become apparent upon reference to the following description of the preferred embodiments, when read in light of the attached drawings.

BRIEF DESCRIPTION OF THE DRAWINGS

FIG. 2 is a partially schematic, sectional view of a pipette constructed in accordance with the invention, for use with the tip of FIG. 1;

FIG. 2A is a fragmentary sectional view similar to a portion of FIG. 2, but of an alternative embodiment;

DESCRIPTION OF THE PREFERRED EMBODIMENTS

The invention is described hereinafter primarily for use in separating portions of a liquid from each other, for example, blood cells from plasma, a preferred embodiment, or substances in a liquid solution, emulsion or dispersion from the rest of the liquid, e.g., from the solvent. That is, whole blood is the preferred two-phase liquid processed by this invention, the denser phase being blood cells and platelets. In addition, the invention is useful in processing other liquids, regardless of the end use that is made of the separated portion. For example, the liquid can be a dispersion of yeast cells, and the desired less dense phase be cell-free culture supernatant. Yet another example is applicable to immunoassays. In some applications, competitive binding allows some labeled antigen to compete with unlabeled patient antigen for sites on an appropriate antibody. After the competitive binding is complete, dextran-coated charcoal is added to the solution, and the mixture is aspirated into the pipette. Following centrifugation within the tip of the pipette, the bound antibody-antigen complex, which is not capable of absorbing onto the charcoal, is the separated supernatant and is dispensed to allow measurement of the amount of bound, labeled antigen.

Yet another preferred use is the separation of cellular components from urine, blood or liquified tissues so that the cells can be lysed or otherwise broken down and its contents, such as DNA, released and processed.

Figure 1:
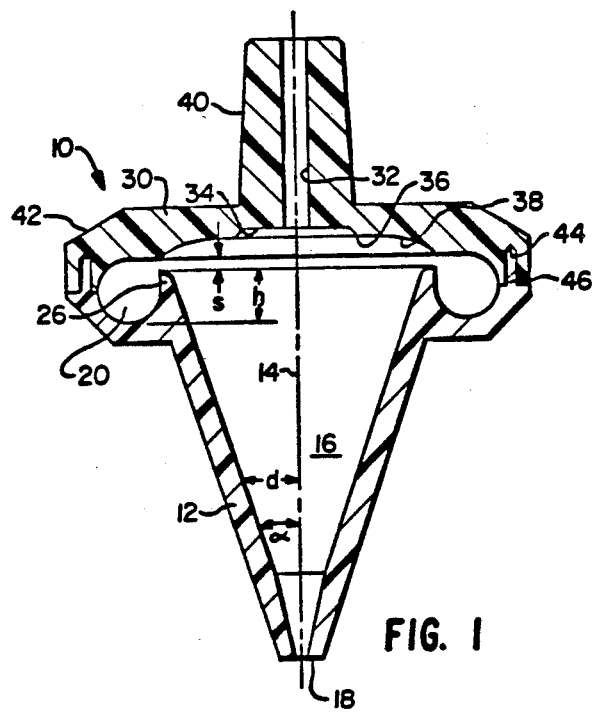
FIG. 1 is a sectional view, taken along an axis of symmetry, of a pipette tip constructed in accordance with the invention.

A pipette tip 10 prepared in accordance with the invention comprises, FIG. 1, a body wall 12 having an axis of symmetry 14, shaped to define a primary or liquid-confining cavity 16. At one end of the tip, wall 12 is provided with an aspirating and dispensing aperture 18 generally centered on axis 14. Wall 12 preferably has a spacing distance "d" from axis 14 that varies along at least a portion of its length (along axis 14). Most preferably, wall 12 is shaped so that "d" increases continuously from its value at aperture 18, to the end of wall 12 forming lip 26 described below, to insure none of the first portion of the liquid, here the dense phase material, gets stuck in cavity 16 during centrifuging, but rather moves into annular trap cavity 20. (The actual angle alpha made by wall 12 against axis 14 can vary widely. A preferred value is about 20°.)

To trap the denser phase during and after centrifuging, annular cavity 20 is wrapped concentrically around axis 14. There is also provided partitioning means, preferably a lip 26, that is an extension of wall 12, for preventing the contents of cavity 20, the denser phase formed by centrifugal force during spinning, from moving into aperture 18. Cavity 20 fluidly connects to cavity 16, by reason of the fact that partitioning lip 26 does not completely close off cavity 20. As used herein, "fluidly connects" means a connection that permits ready passage of a liquid between the two sections or compartments. Specifically, spacing "s" is from about 250 μm (0.010") to about 500 μm (0.020"), and most preferably about 380 μm (0.015"). Cavity 20 has a volume sufficient to hold all of the denser phase. The exact amount differs, of course, depending on the planned use of the tip. For trapping blood cells of a volume of 200 μl of whole blood contained in cavity 16, the trap volume is about 100 μl, to accommodate "worst hematocrit" cases.

Most preferably, lip 26 is provided at the end of wall 12 opposite to the end with aperture 18. Like cavity 20, it preferably extends circumferentially completely around axis 14. Its height "h" is sufficient to retain the denser, trapped phase against flow back into cavity 16 under the influence of gravity when axis 14 is vertical. The exact value of h will vary, depending on the volume of cavity 20. Preferably, h has a value of between about 1 to about 2.0 mm, and most preferably about 1.5 mm, when used with 200 μl of whole blood.

In a highly preferred example, the total height of cavity 16, from aperture 18 to the top of lip 26, is about 1.2 cm.

The top of cavity 20 is formed by top wall 30, which has an air passage 32 extending out therethrough at axis 14. Preferably, a recess 34 is formed concentrically surrounding passage 32, so as to create a sharp edge 36. Edge 36 acts to keep separated less dense phase from creeping along wall 30 back onto recess 34 so as to retard drainage down into the bottom of cavity 16 after rotation stops. In addition wall 30 is preferably rounded at portion 38, to eliminate sharp corners that could prevent the denser phase from flowing smoothly into cavity 20 during centrifuging.

Nipple 40 extends out the top of wall 30, concentrically around passage 32, to permit ready mounting of the tip in a pipette.

To render tip 10 readily moldable out of plastics, preferably wall 30 is formed as a separate member 42 with an annular groove 44 near its outermost circumference. A mating annular lip 46 is formed in the remaining part of the tip, to mate with groove 44 and form a leak-tight seal.

Tip 10 can be used with any pipette, including manual pipettes. To achieve separation within the tip, the pipette preferably mounts nipple 40 in an air-tight mount, and permits tip 10 to rotate continuously at high speed.

A preferred form of such a pipette 50 is illustrated in FIG. 2. Such a pipette comprises a frame 52, a handle portion 54 of the frame, push-button controls 56, a display 58, a pressurizing and evacuating chamber 60, a piston 62 movable within the chamber to create a pressure or a partial vacuum, respectively; motor means 64 for actuating the piston, for example, one available from Airpax Corp., owned by North American Philips Company, under the trade name "Airpax Linear Actuator L92100", an air passage 66 extending from chamber 60, a passageway 68 extending from passage 66, and means 70 for disconnecting passage 66 from passageway 68, for example, a disconnect lever 72 actuated by pull rod 74 against a return spring 76. Rod 74 in turn bears on the end of lead screw 75, that travels the same direction and distance as piston 62. When rod 74 is released, spring 76 contracts to pull end 77 of passage 66 into sealed engagement with the end of passageway 68. Additionally, a microprocessor, not shown, is included to control the functions of the pipette, utilizing power from a line 78 extending out an umbilical cord 80.

All of the preceding are individually conventional, and require no further description.

To mount tip 10 on the pipette, a chuck 84 is provided, centered on axis 14 which coincides with the long axis of the pipette. Chuck 84 is in turn integrally connected to passageway 68 that fluidly connects passageway 32 of tip 10, FIG. 1, with passage 66 of the pipette. To permit chuck 84 to rotate continuously, tubular passageway 68, and thus the chuck, are rotatably mounted withing bearings 86 and 88. To provide such rotation at speeds of preferably from 30,000 to 100,000 RPM, an electric motor or air turbine 90 is mounted on passageway 68. The air turbine is powered by an air supply, which can be off-pipette and connected to turbine 90 by an air hose 92, or it can be mounted within frame 52. The air turbine is conventional, and is the type that generates up to 100,000 RPM or more for light-weight loads. Examples can be found in high-speed dental drills.

Optionally, a tip ejector 100 is also included, comprising a yoke 102 mounted on arm 104. Arm 104 in turn is pivotally attached to frame 52 at one end 106, and at its other end 108, to an actuating lever 110. Such lever is manually actuated at handle 54 by means, not shown.

The mounting of tip within chuck 84 need not be a male-female connection as shown in FIG. 2. Alternatively, it can be a female-male configuration as shown in FIG. 2A, wherein nipple 40 is replaced by a collar 40a. Parts similar to those previously described bear the same reference numeral, to which the distinguishing suffix a is applied. Thus collar 40a of tip 10a is now the female part, and chuck 84a is a male member with passageway 68a extending through it. The advantage of such a construction is that collar 40a can be more readily used to collect whole blood directly, as from a finger prick, than can nipple 40.

Alternatively, the pipette can be contructed so that no air disconnect is needed when spinning is desired. This is accomplished, not shown, by mounting the dispensing motor so that its output is connected to a DC motor used to spin the chuck. That is, the DC motor advances and withdraws, as demanded by the dispensing motor. The drive shaft of the DC motor in turn is attached to the piston of a piston chamber, and the piston is splined to that chamber. The chamber is integrally connected to the chuck. Thus, when the DC motor is advanced per the dispensing motor, it pushes the piston relative to the piston chamber, which cannot reciprocate. But when the DC motor spins its drive shaft, the entire assembly of the piston and chamber spins, as does the chuck. (The bearings in this case encase the piston chamber and piston as well.)

Figure 3A:
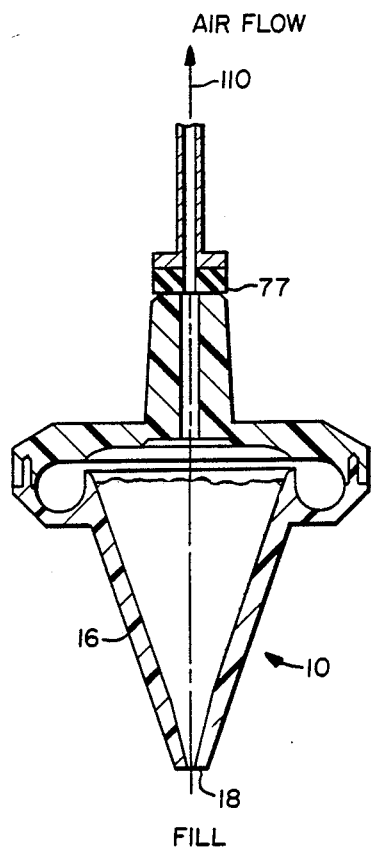
FIGS. 3A-3D are fragmentary sectional views similar to that of FIG. 1, illustrating one manner of use of the pipette and pipette tip.
Figure 3B:
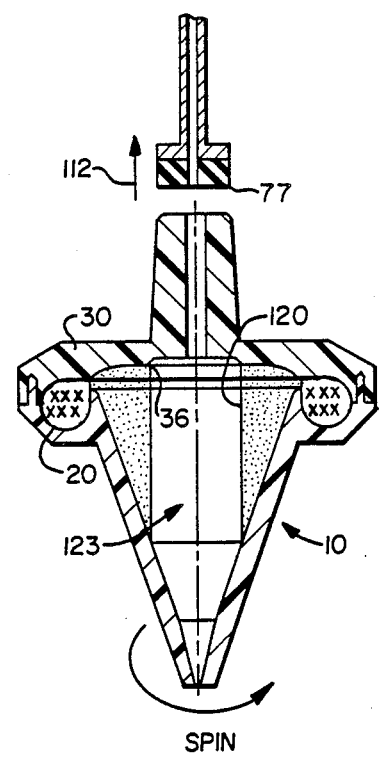
Figure 3C:
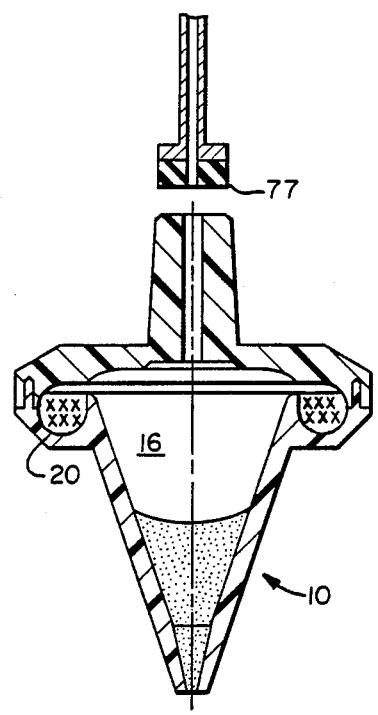
Figure 3D:
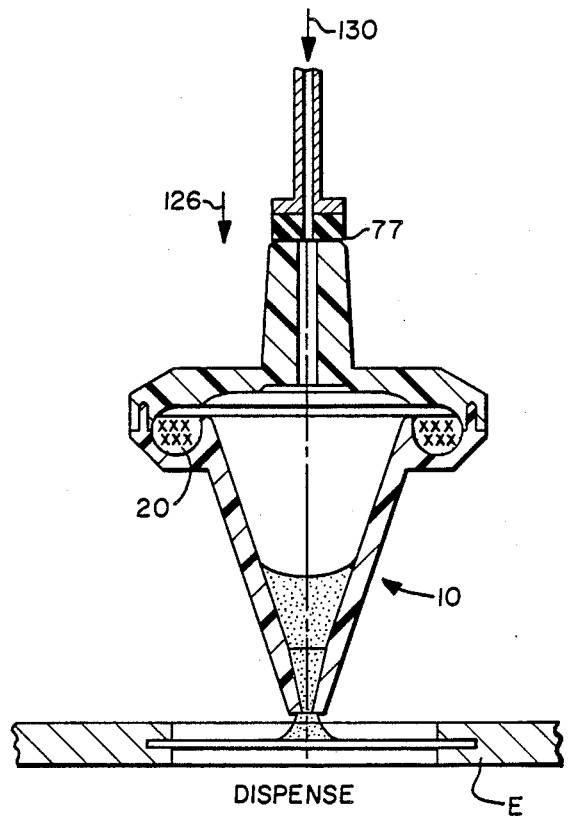

The manner of use of the pipette tip and pipette will be readily apparent from the preceding discussion. As a further aid in understanding, reference is made to FIGS. 3A–3D. To aspirate into the tip the liquid with the two phases, e.g., whole blood, end 77 of the passage 66 is allowed to contact passageway 68, and thus make fluid contact with the interior of tip 10. In FIG. 3A, this is symbolized by end 77 making direct contact with the pipette tip, rotatable passageway 68 being omitted in all of FIGS. 3A–3D for clarity. Piston 62 is then withdrawn to created a partial vacuum, as indicated by arrow 111, and the liquid is drawn up to substantially fill, but not overfill, cavity 16. If what is aspirated is whole blood from a finger prick, it is preferable that an anti-coagulant be pre-coated on the inside of the tip. At this stage, rod 74 is forced against spring 76 by screw 75, to pull end 77 away from passageway 68, arrow 112 of FIG. 3B, to permit passageway 68, chuck 84 (FIG. 2) and tip 10 to be rotated at high speed to cause the denser phase, shown in cross-hatching, to flow into cavity 20, leaving the less dense phase alone in cavity 16. (Before spinning, surface tension retains liquid in cavity 16 from spilling out of aperture 18). While spinning, the meniscus 120 of the less dense phase leaves a temporary hollow passageway 123 centered on axis 14 that is free of liquid. In this manner, cavities 16 and 20 act together as a blood separation compartment, lip 26 being effective in maintaining separation of the denser phase from the less dense. Thus, FIG. 3C, when spinning ceases, the dense phase is confined to cavity 20 and edge 36 retards any tendency of the less dense phase to migrate across the surface 34. Thus, the less dense phase collapses to eliminate passageway 123 and to move adjacent aperture 18 where it is ready for dispensing onto a test element E, as is shown in FIG. 3D. This last step is accomplished by rod 74 releasing end 77, arrow 126, to allow fluid connection with the tip interior, so that pressure, shown as arrow 130, generated in pipette chamber 60, FIG. 2, is effective to dispense fractions of the less dense phase.

After dispensing is completed, the tip is removed using ejector yoke 102, FIG. 2, and disposed of.

When used to process whole blood, the pipette tip and pipette of this invention have been found to effectively separate plasma from cells as follows, for a preferred embodiment:

| Spinning Time (Sec) | RPM of Separation |
| --- | --- |
| 40 | 30,000* |
| 23 | 40,000 |
| 15 | 50,000 |
| 10 | 60,000 |
| 8 | 70,000 |
| 6 | 80,000 |
| 5 | 90,000 |

| Spinning Time (Sec) | RPM of Separation |
|---|---|
| 4 | 100,000 |

*This is the only one of this table that was actually measured. The remainder were calculated on the basis of the ratio of the square of the RPM.

It will thus be readily apparent that the centrifuging step is largely user transparent. That is, the user pushes button 56, FIG. 2, to start the process which begins with centrifuging. This can take as little as 4 seconds. Pushing the button a second time cycles the pipette through the dispensing steps, which can be easily coordinated with movement of test elements through the analyzer. Waiting 4 seconds to do the second step is considered to be a transparent involvement of the user. Alternatively, the process can be entirely automatic after the pushing of button 56 the first time, by using two-way communication between the pipette and the analyzer, such as via an infra-red or ultrasonic beam emitted and received by each of the pipette and analyzer using conventional equipment.

The previous embodiments utilize a high speed electric spinning means or air supply for spinning that is supplied via the pipette. Alternatively, such can be supplied by the analyzer, FIG. 4. Such an analyzer comprises several stations, the essential ones of which are a liquid dispensing station 210 and a read station 230. Any convenient means 240 are useful in advancing a test element E' from one station to the next, e.g., such as those described in U.S. Pat. No. 4,303,611, issued on 12/1/81.

Figure 4:
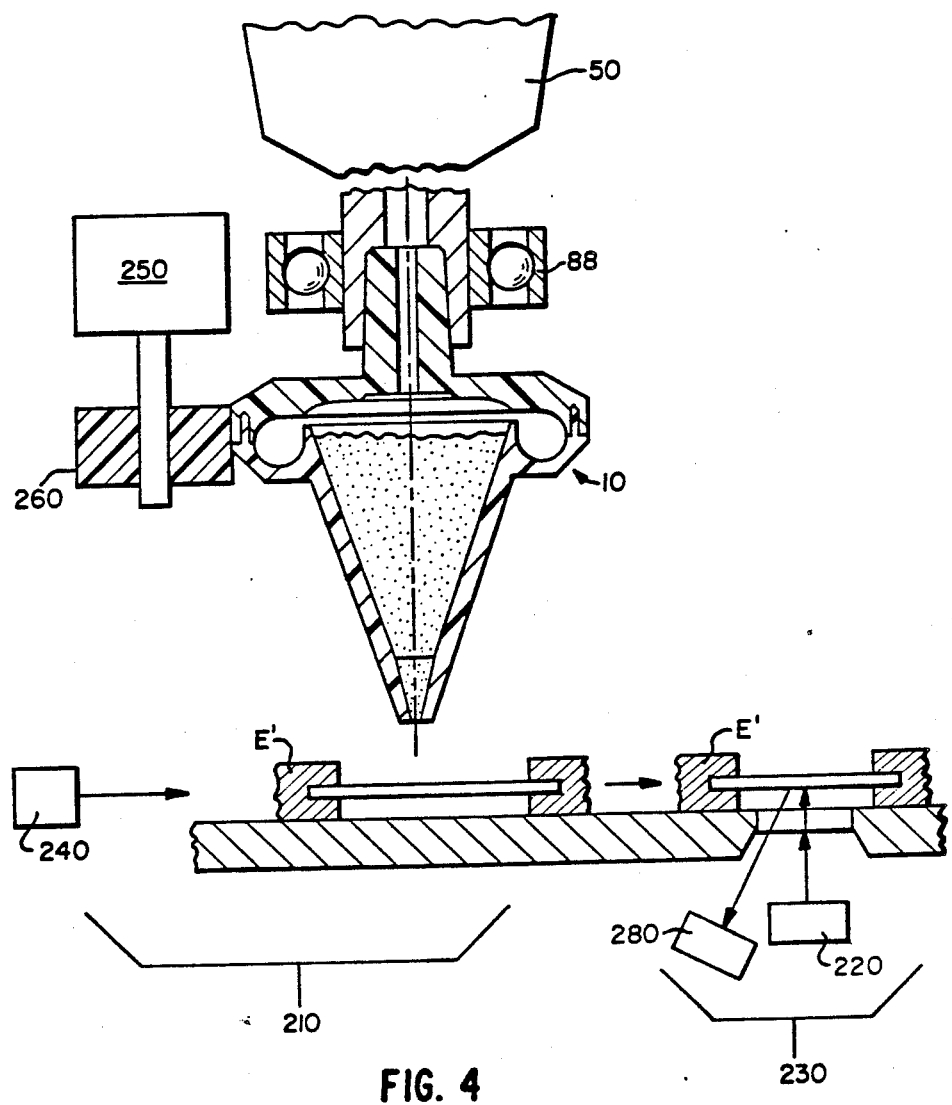
FIG. 4 is a partially schematic, fragmentary sectional view of an improved analyzer constructed in accordance with the invention.

At station 210, a pipette 50, shown schematically in FIG. 4, is supported by suitable conventional means, not shown. The first step in the process of dispensing plasma occurs when whole blood is aspirated. Thereafter, a conventional motor 250, e.g., a DC motor that is part of the analyzer at station 210, rapidly rotates a suitable drive wheel, such as a capstan roller 260, that bears against, for illustration, the circumference of tip 10, preferably at its largest portion. Because tip 10 is free because of bearing 88 to rotate continuously and at high speed, separation of the two phases occurs in the tip in the same manner as described for the previous embodiments.

A detectable change is then read, after suitable incubation, at read station 230. Such station can use, e.g., a light source 220 and a detector 280 oriented on 90°–45° axes, as is conventional.

Figure 5:
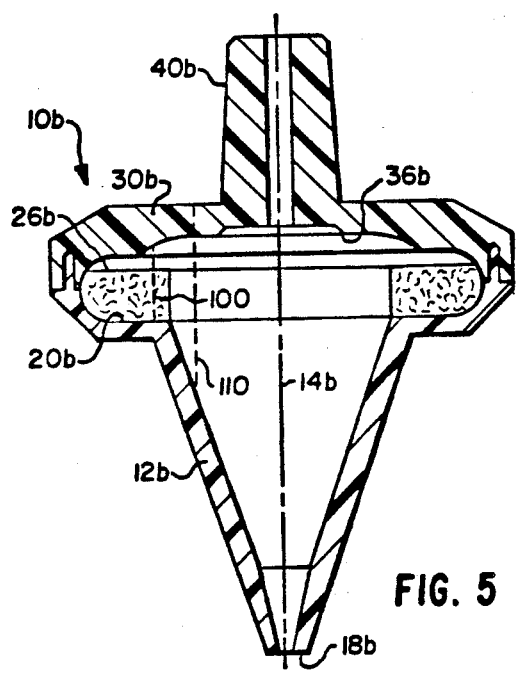
FIG. 5 is a sectional view similar to that of FIG. 1, but of an alternate embodiment.

The partitioning means for maintaining the separation of the two liquid phases need not be an extension of body wall 12. FIG. 5 illustrates an embodiment in which the partitioning means is a gel with a specific gravity inbetween that of the two liquid phases being separated. Parts similar to those previously described bear the same reference numerals, to which the distinguishing suffix "b" is appended.

Thus, the configuration of tip 10b is identical to that of FIG. 1, except that the lip is replaced by gel 26b. This gel can be any material that is non-toxic to and non-destructive of the liquid phases, with a specific gravity that is between about 1.03 and 1.06 if the liquid to be separated is whole blood. Useful examples are described in, e.g., U.S. Pat. No. 4,050,451, and are conventional for maintaining the separation of the two phases of whole blood after centrifuging.

During the spinning of tip 10b, gel 26b tends to be displaced out of trap cavity 20b by the blood cells, so as to flow towards axis 14b. When spinning is finished, it occupies generally the space between the vertical dotted lines 100 and 110. The less dense phase (plasma in the case of whole blood) is then positioned between line 110 and axis 14b.

Alternatively, instead of being positioned initially in cavity 20b, the gel can be disposed along wall 12b as a thin coating that does not plug up aperture 18b.

When using gel 26b as the partitioning means, there is no need to provide edge 36b in upper portion 30b, since the gel prevents streaming of cells across the top. Accordingly, edge 36b is optionally eliminated (not shown) in this embodiment.

Figure 6:
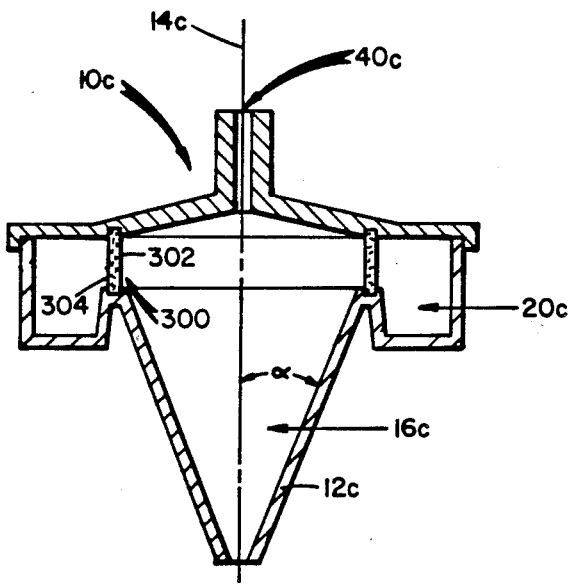
FIG. 6 is a sectional view similar to that of FIG. 1, but illustrating still another embodiment.
Figure 7:
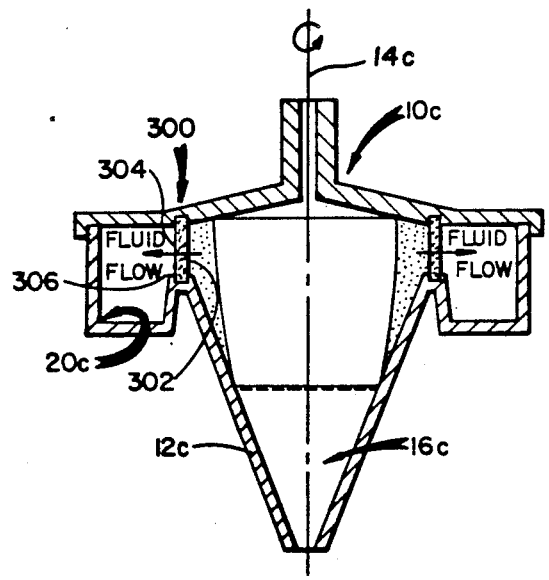
FIG. 7 is a section view similar to that of FIG. 6, illustrating a preferred use.
Figure 8:
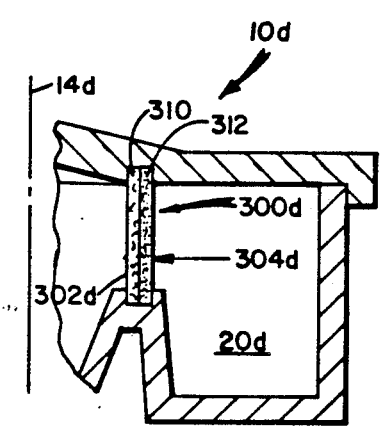
FIG. 8 is a fragmentary section view of a tip similar to that of FIG. 6, except yet another embodiment is illustrated.

In the embodiments of FIGS. 6–8, a filter is used in place of a lip or gel, as the means for separating, and maintaining separate, a substance of the liquid from the rest of the liquid during spinning. In these embodiments, the separation is not based upon density of the components. Rather, it is based upon the use of the filter to separate one component from the rest, either physically via pore size selection, or chemically via bonding to chemicals on the filter. Parts similar to those previously described bear the same reference numeral, to which the distinguishing suffix "c" is appended.

Thus, FIG. 6, a pipette tip 10c is prepared as in the previous embodiments, with a body wall 12c extending around an axis of symmetry 14c, providing the primary liquid-confining cavity 16c. A trap cavity 20c is also provided, shaped similarly as in the previous embodiments. Nipple 40c also functions as described above.

Unlike the previous embodiments, filter 300 is used in lieu of lip 26, FIG. 1, approximately in the same location as such lip. The filter completely closes off liquid access from cavity 16c to cavity 20c, except through the pores of the filter. To that end, the filter is preferably an annulus extending completely around axis 14c as shown, although other shapes approximating an annulus are also useful. Any filter material is useful, such material being selected with a pore size and of a composition suitable for the intended filtration. Most preferably, the composition provides a weakly hydrophobic surface at surfaces 302 and/or 304, and a membrane intrusion resistance that is less than the centrifugal force developed by the liquid when tip 10c is spun. In addition, the pore sizes are selected to retain cellular or other materials contained in the body fluid comprising the liquid. A 10u Polycarbonate filter manufactured by Nucleopore is a useful example of such filter composition.

In use, FIG. 7, tip 10c is spun about axis 14c, as indicated and as described above, causing the liquid to press against filter 300. Such liquid pressure overcomes the membrane intrusion resistance and hydrophobicity at surfaces 302 and 304, so that the liquid filters through into cavity 20c. Most preferably, therefore, cavity 20c is large enough to accommodate, when tip 10c is not spinning, all of the liquid previously confined in cavity 16c, below the rim 306 of wall 12c where it would otherwise contact filter 300 if higher in level. Alternatively, the amount of liquid aspirated into tip 10c prior to spinning is adjusted to ensure that it will all go into cavity 20c below the rim 306.

As surface 304 dries out, its weakly hydrophobic nature becomes restored enough to resist any splashing of liquid in cavity 20c, from penetrating back to surface 302.

What is retained on surface 302 are cellular products and particulates that are larger than the pores of filter 300. For example, leukocytes of blood are retained if the filter pore sizes are no larger than about 8-10 microns.

Thereafter, additional processing liquid is aspirated into cavity 16c, for example a cellular lysis liquid such as a solution of quinidinium isothiocyanate, to react with the retained matter on surface 302. For example, that processing liquid can be used to extract DNA from leukocytes. The processing liquid is brought into contact with surface 302 by slowly spinning tip 10c at greatly reduced speeds. Such reduced speeds are selected so that the centrifugal force is less than that needed to overcome the membrane intrusion resistance of filter 300. As a result, contents lysed from cells trapped at surface 302 are not forced or carried through the filter to cavity 20c. Instead, they are retained in cavity 16c for subsequent dispensing.

Thus, tip 10c can be used to separate out particulate or cellular material from the liquid in a solution, emulsion, or dispersion.

Alternatively, FIG. 8, the filter can be a composite material. Parts previously described bear the same reference numeral to which the distinguishing suffix "d" is appended. Thus, tip 10d is constructed generally as is described for the embodiment of FIGS. 6 and 7, except that filter 300d is a composite material. More precisely, there are two annular rings 310 and 312 laminated together, with ring 310 separating ring 312 from axis 14d. Examples of ring 310 include chemically treated membranes such as "Nylon 66", and of ring 312, include a woven hydrophobic material such as "Teflon". Such materials are selected because the pores of ring 310 are best suited to trap and retain the particulate desired, without necessarily having the necessary resistance to back pressure generated by the liquid in cavity 20d washing onto surface 304d. Ring 312, on the other hand, is adapted to resist such back-washing, without regard to pore sizes particularly needed to trap the particulates.

Yet another embodiment features the filter and tip construction of the embodiment of either FIG. 6 or FIG. 8, but wherein a chemical bond is used, rather than critical pore sizes and physical separation, to separate a selected component from the liquid solution, emulsion or dispersion. In such cases a bonding agent is attached to surface 302 or 302d, to bond directly to the components to be separated, or to a chemical on such component. Therefore, the pore sizes of filter 300 or 300d is of no concern in such an arrangement.

Specific examples of this embodiment include a filter impregnated with avidin, used to separate out from the rest of the liquid a biotinylated DNA probe. (The rest of the liquid passes through to the cavity 20c or 20d.) The bond of the probe to the filter can be subsequently broken by aspirating into cavity 16c or 16d, a small quantity of a chaotropic agent used, for example, in affinity chromatography, and then spinning tip 10c or 10d slowly to cause wetting of surface 302 or 302d. (Such a technique for breaking such a bond is described in the prior literature.) Still other examples are filters coated with polyclonal or monoclonal antibodies that specifically bind to an antigen of choice, or filters impregnated with iminobiotin that bond at the imino group with a substance carrying an avidin group. The antibody-antigen bond, following separation, can be broken for retrieval of the antigen by treating surface 302 or 302d, as previously described. The bond between the iminobiotin and avidin can be subsequently broken, after separation, by aspirating a buffer such as a mixture of sodium acetate and acetic acid having a pH of 4, and spinning the tip slowly to lower the pH of surface 302 or 302d until the bond is broken, as is well-known.

Figure 9:
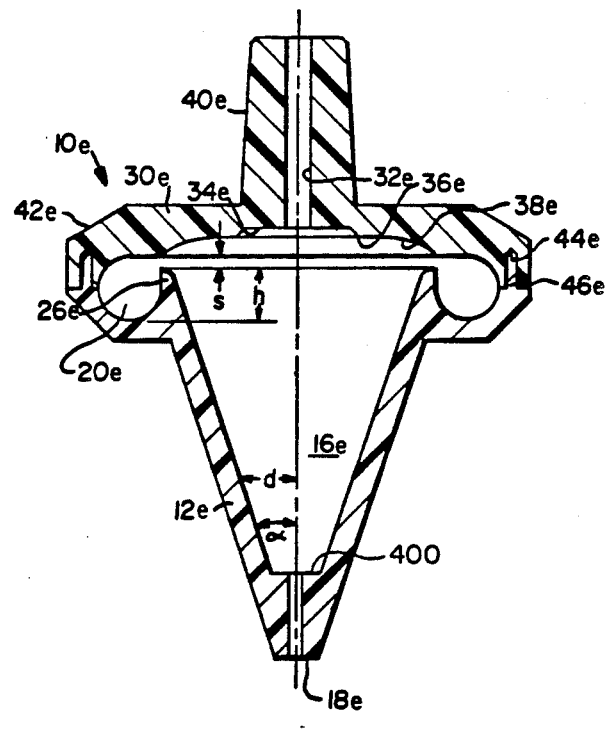
FIG. 9 is a section view similar to FIG. 1, but of still another alternate embodiment.

In some instances, there may be a tendency of the separated lighter phase to fall out the aperture, once spinning has ceased. In such a case, the alternate embodiment of FIG. 9 is useful, in which a ledge 400 is provided adjacent aperture 18e. (Parts similar to those previously described bear the same reference numeral, to which the distinguishing suffix "e" is appended. Ledge 400 is located in a plane that is preferably perpendicular to axis 14e. That is, the plane of ledge 400 preferably makes an angle to wall 12e that is 90°+α). Any angle much less than this will tend to trap air at the pocket formed by the ledge, an undesirable feature. The remaining features of the tip 10e (16e, 20e, 26e, 30e, 32e, 34e, 38e, 40e, 42e, 44e, 46e) are the same as for the embodiment of, e.g., FIG. 1.

The invention has been described in detail with particular reference to preferred embodiments thereof, but it will be understood that variations and modifications can be effected within the spirit and scope of the invention.

What is claimed is:

1. A pipette tip capable of separating portions of a liquid solution, emulsion or dispersion said tip comprising
   means for mounting the tip within a pipette,
   a body wall disposed about an axis of symmetry to define a liquid-confining cavity of the tip,
   means defining a dispensing aperture in said body wall,
   and separating means for separating, and maintaining separate, a first portion of the liquid solution, emulsion or dispersion from a second portion when the tip is spun about said axis of symmetry.

2. A tip as defined in claim 1, wherein said separating means extends concentrically and entirely around said axis of symmetry.

3. A tip as defined in claim 1, wherein said separating means includes a trap cavity and partitioning means for keeping the first portion contained within said trap cavity, said body wall being shaped to direct liquid flow towards said trap cavity during spinning.

4. A tip as defined in claim 3, wherein said partitioning means is a lip that extends from said body wall, and the first portion is the denser of two portions of the liquid solution, emulsion or dispersion.

5. A tip as defined in claim 3, wherein said separating means includes a filter completely closing off said trap cavity from said liquid-confining cavity, except for pores in said filter.

6. A tip as defined in claim 5, wherein said filter is constructed with pore sizes selected to pass liquid through the filter and to retain particulate or cellular matter contained in the liquid.

7. A tip as defined in claim 5, wherein said filter is chemically treated to bind the second portion and to allow the first portion to pass through to said trap cavity, and wherein the second portion is a selected component of the solution, emulsion or dispersion.

8. A tip as defined in claim 5, wherein said filter is an annulus.

9. A pipette tip capable of separating two different-density phases of a two-phase liquid, said tip comprising
   a body wall disposed about an axis of symmetry to define a primary cavity of the tip, the wall having a varying spacing distance from said axis along at least a portion of the length of said wall, means defining a dispensing aperture in said body wall, said spacing distance of said wall increasing with increased distance from said aperture, a trap cavity fluidly connected to said primary cavity and extending concentrically around said axis, said trap cavity having a volume less that the volume of said primary cavity but sufficient to hold substantially all of the denser of said two phases, said trap cavity being disposed on said body wall spaced along said axis away from said dispensing aperture, the portion of said body wall extending between said dispensing aperture and said trap cavity being shaped to have a slope relative to said axis that is sufficient to force substantially all of said denser phase to flow into said trap cavity when said tip is spun about said axis, and a partitioning lip extending concentrically around said axis between said primary cavity and said trap cavity, said lip having a height measured parallel to said axis sufficient to prevent gravity flow of collected denser phase out of said trap cavity and into said primary cavity when said axis is vertical.

10. A pipette tip as defined in claim 9, and further including means thereon for engaging a high speed spinning means.

11. In a pipette for aspirating and dispensing a liquid and having a fluid passageway cooperating with a pipette tip, first means for evacuating and pressurizing said fluid passageway for filling and dispensing the liquid from the tip, and means for removably mounting the tip, the improvement wherein said mounting means is constructed to permit the tip to rotate continuously at high speed about an axis of symmetry thereof.

12. A pipette as defined in claim 11, and further including means for rotating said mounting means or the tip at high speed.

13. In a combination comprising a pipette having an axis and comprising a fluid passageway and first means for evacuating and pressurizing said fluid passageway, and a removable pipette tip connected to said passageway for collecting and dispensing liquid in response to said first means for evacuating and pressurizing, the improvement wherein said pipette further includes means for mounting said tip to rotate continuously on said pipette about said axis, and wherein said tip includes means for separating, and maintaining separate, a portion of the liquid contained therein centrifugally separated from the remainder in response to spinning at high speeds about said axis.

14. A combination as defined in claim 13, and further including means in said pipette for spinning said tip at high speeds about said axis.

15. In an analyzer comprising a first station constructed to dispense a body liquid onto a test element using a pipette provided with a pipette tip, a second read station including means for detecting a change in the test element in response to the body liquid, and means for transporting the test element from one of said stations to the other, the improvement wherein said first station includes means for spinning said pipette tip at high speeds about an axis of symmetry of said tip.

16. A method of separating two portions of a liquid solution, emulsion or dispersion in a pipette, comprising the steps of (a) aspirating the liquid solution, emulsion or dispersion into a tip comprising means for mounting the tip within a pipette, a body wall disposed about an axis of symmetry to define a liquid-confining cavity of the tip, means defining a dispensing aperture in said body wall, and separating means for separating, and maintaining separate, a first portion of the liquid solution, emulsion or dispersion from a second portion when the tip is spun about said axis of symmetry, said tip being mounted on the pipette, and (b) spinning the tip to force a portion of the liquid solution, emulsion or dispersion past said separating means.

* * * * *